US010018590B2

(12) United States Patent
Mahavadi et al.

(10) Patent No.: US 10,018,590 B2
(45) Date of Patent: *Jul. 10, 2018

(54) CAPILLARY ELECTROPHORESIS FOR SUBTERRANEAN APPLICATIONS

(71) Applicant: Schlumberger Technology Corporation, Sugar Land, TX (US)

(72) Inventors: Sharath Chandra Mahavadi, Edmonton (CA); Geza Horvath Szabo, Novosibirsk (RU); Simon Ivar Andersen, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 497 days.

This patent is subject to a terminal disclaimer.

(21) Appl. No.: 13/968,221

(22) Filed: Aug. 15, 2013

(65) Prior Publication Data

US 2015/0047979 A1 Feb. 19, 2015

(51) Int. Cl.
*G01N 27/447* (2006.01)
*E21B 49/08* (2006.01)

(52) U.S. Cl.
CPC ..... *G01N 27/44743* (2013.01); *E21B 49/087* (2013.01)

(58) Field of Classification Search
CPC . G01N 27/447–27/44791; E21B 47/00; E21B 47/0007; E21B 47/01; E21B 47/12–47/124; E21B 49/02; E21B 49/08–49/083; E21B 49/087–49/10
See application file for complete search history.

(56) References Cited

U.S. PATENT DOCUMENTS

| 5,141,621 | A | 8/1992 | Zare et al. |
| 5,269,901 | A | 12/1993 | Dill et al. |
| 5,297,420 | A | 3/1994 | Gilliland et al. |
| 5,312,535 | A | 5/1994 | Waska et al. |

(Continued)

FOREIGN PATENT DOCUMENTS

| EP | 0339780 B1 | 11/1989 |
| EP | 1909099 A1 | 4/2008 |

(Continued)

OTHER PUBLICATIONS

International Search Report and the Written Opinion for International Application No. PCT/US2014/051208 dated Dec. 23, 2014.

(Continued)

*Primary Examiner* — J. Christopher Ball
(74) *Attorney, Agent, or Firm* — Bridget M. Laffey

(57) ABSTRACT

A method of fluid testing includes pressurizing a fluid testing system, disposed at a subterranean location under high pressure compared to a surface pressure, to achieve a desired pressure differential between the high pressure and an internal pressure of the fluid testing system. The fluid testing system includes a capillary electrophoresis system and one or more test fluid reservoirs. The method also includes directing test fluid from the one or more test fluid reservoirs into capillaries to condition the capillaries. The method further includes directing sample fluid into the capillaries for testing while at the subterranean location.

39 Claims, 6 Drawing Sheets

(56) References Cited

U.S. PATENT DOCUMENTS

| | | | |
|---|---|---|---|
| 5,584,982 | A | 12/1996 | Dovichi et al. |
| 5,667,657 | A | 9/1997 | Recknor et al. |
| 5,675,155 | A * | 10/1997 | Pentoney, Jr. ......... G01N 27/44721 204/452 |
| 5,885,430 | A | 3/1999 | Keman et al. |
| 5,916,428 | A | 6/1999 | Kane et al. |
| 5,972,187 | A | 10/1999 | Parce et al. |
| 6,531,041 | B1 | 3/2003 | Cong et al. |
| 6,939,717 | B2 | 9/2005 | Jiang et al. |
| 7,231,819 | B2 | 6/2007 | Jones et al. |
| 7,364,705 | B2 | 4/2008 | Sundberg et al. |
| 7,381,317 | B2 | 6/2008 | Liu et al. |
| 7,857,955 | B2 | 12/2010 | Ratnayake et al. |
| 8,340,913 | B2 | 12/2012 | Mostowfi et al. |
| 8,485,026 | B2 | 7/2013 | Mostowfi |
| 8,881,577 | B1 * | 11/2014 | Agar ................... E21B 49/005 73/54.06 |
| 2002/0179532 | A1 | 12/2002 | Citterio et al. |
| 2003/0000838 | A1 | 1/2003 | Yeung et al. |
| 2003/0013147 | A1 | 1/2003 | Hildenbrand |
| 2003/0052008 | A1 | 3/2003 | Liu et al. |
| 2003/0116436 | A1 | 6/2003 | Amirkhanian et al. |
| 2003/0116438 | A1 | 6/2003 | Yamazaki et al. |
| 2003/0196896 | A1 * | 10/2003 | McWaid .......... G01N 27/44704 204/455 |
| 2004/0045350 | A1 * | 3/2004 | Jones .................. E21B 43/38 73/152.23 |
| 2007/0111329 | A1 | 5/2007 | Guzman |
| 2009/0150087 | A1 | 6/2009 | Steinecker |
| 2009/0159288 | A1 | 6/2009 | Horvath Szabo et al. |
| 2009/0294175 | A1 * | 12/2009 | Cartellieri ............ E21B 47/10 175/50 |
| 2015/0114837 | A1 | 4/2015 | Mahavadi |

FOREIGN PATENT DOCUMENTS

| | | |
|---|---|---|
| WO | 9510344 A1 | 4/1995 |
| WO | 0163094 A1 | 8/2001 |
| WO | 0173424 A1 | 10/2001 |
| WO | WO0198630 A1 | 12/2001 |
| WO | WO02059589 A2 | 8/2002 |
| WO | WO03010528 A1 | 2/2003 |
| WO | 2013062879 A1 | 5/2013 |

OTHER PUBLICATIONS

M.I. Al-Katheeri and H.A. Nasr-El-Din, SPE, Saudi Aramco, "Application of CE and CE-MS to Assay Corrosion Inhibitors Used in Well-Stimulation Treatments," SPE 95112, SPE International Symposium on Oilfield Corrosion held in Aberdeen, United Kingdom, May 13, 2005.

International Preliminary Report on Patentability issued in the related PCT application PCT/US2014/051208, dated Feb. 16, 2016 (7 pages).

Stella Rovio, Kimmo Sirén, Heli Sirén, —Application of capillary electrophoresis to determine metal cations, anions, organic acids, and carbohydrates in some Pinot Noir red wines—Food Chemistry, (2011) 124, 1194-1200 (7 pages).

Norman J. Dovichi, DNA Sequencing by Capillary electrophoresis, Electrophoresis 1997, 18, 2393-2399 (7 pages).

Kok, W.T.; Tudo, A.J.; Grutters, M.; Shepherd—Characterization of Asphaltenes by Nonaqueous Capillary Electrophoresis—A.G. Energy & Fuels, 2011, 25, 208-214 (7 pages).

International Search Report and the Written Opinion issued in the related PCT application PCT/US2013/045589, dated Nov. 27, 2013 (13 pages).

International Preliminary Report on Patentability issued in the related PCT application PCT/US2013/045589, dated Jan. 20, 2015 (9 pages).

Examination Report received in the related GC Application GC/2013/24951, dated Nov. 20, 2016 (5 pages).

Search Report issued in the EP Application 13819418.8, dated Jan. 30, 2017 (5 pages).

Office Action issued in the EP Application 13819418.8, dated Mar. 15, 2017 (11 pages).

\* cited by examiner

CAPILLARY ELECTROPHORESIS FOR SUBTERRANEAN APPLICATIONS

BACKGROUND

Analyzing hydrocarbon fluids provides insight into hydrocarbon fluid reservoir potential. Data from the analysis can be useful in understanding the quality and economic value of produced fluids from the reservoir. In some applications, the composition of water produced or injected is analyzed to improve controls in flow assurance. The produced or injected water may contain a variety of organic and inorganic anions and cations that may be subjected to the analysis. The fluids may be analyzed at the wellhead or in a laboratory, although the results of surface-based analyses may vary in accuracy because conditions at the surface may be different from conditions at the subterranean location.

SUMMARY

The present disclosure relates to a method of fluid testing that includes pressurizing a fluid testing system, disposed at a subterranean location under a high pressure compared to a surface pressure, to achieve a desired pressure differential between the high pressure and an internal pressure of the fluid testing system. The fluid testing system includes a capillary electrophoresis system and test fluid reservoirs. The method also includes directing test fluid from the test fluid reservoirs into capillaries to condition the capillaries. The method further includes directing sample fluid into the capillaries for testing while at the subterranean location.

The present disclosure also relates to a fluid testing system that includes a capillary electrophoresis system and test fluid reservoirs in fluid communication with the capillary electrophoresis system. The capillary electrophoresis system includes capillaries designed to receive a sample fluid. The test fluid reservoirs each include a pressure balancing feature. The fluid testing system also includes a chamber enclosing the capillary electrophoresis system and enabling application of pressure to the capillary electrophoresis system and the test fluid reservoirs.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

Figure 1:
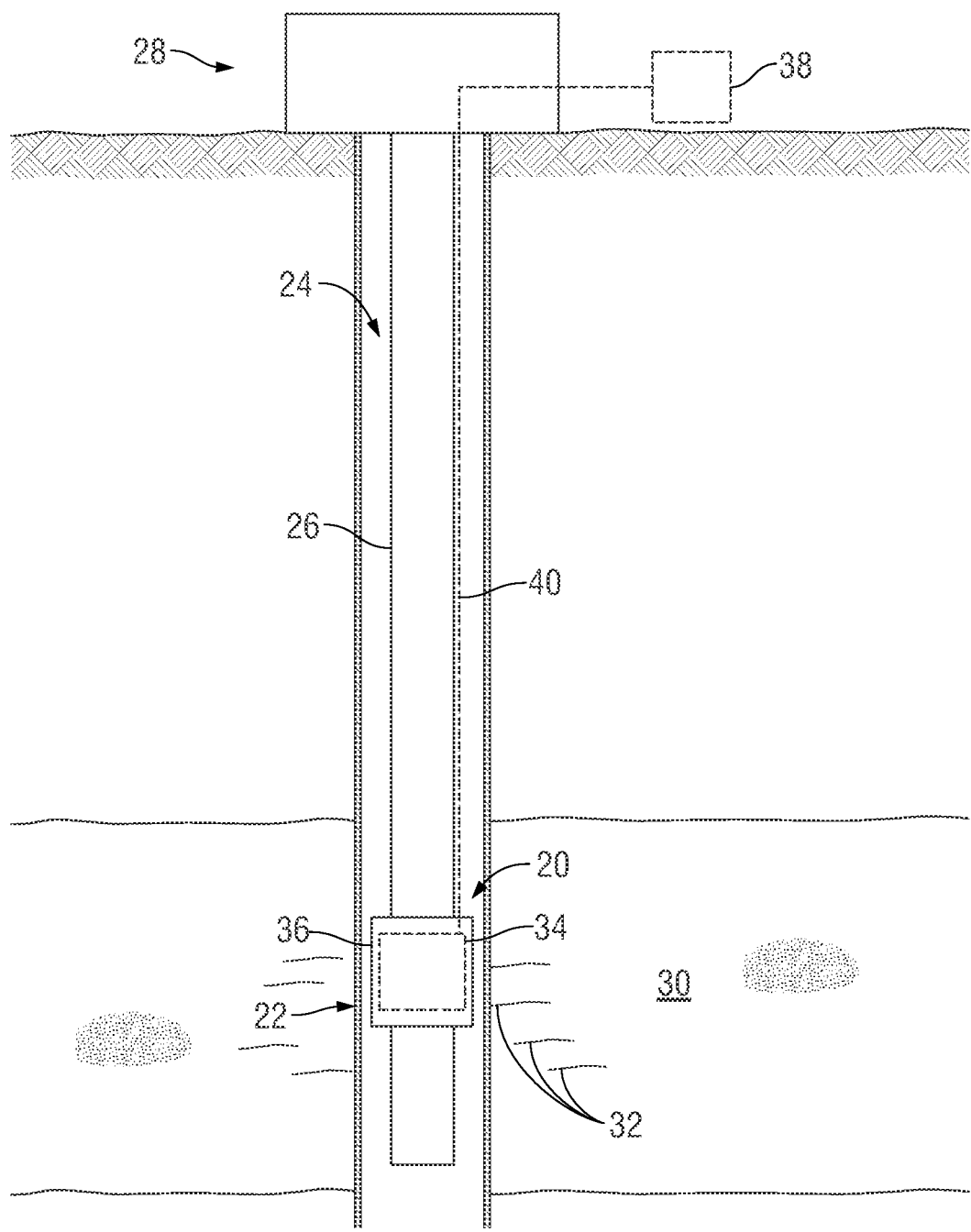
FIG. 1 is a schematic illustration of an example of a subterranean fluid testing system deployed at a subterranean location, according to an embodiment of the disclosure.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a system and methodology for testing of fluids in situ at a subterranean environment. In some applications, for example, testing is performed at a subterranean formation to facilitate analysis of fluids in the subterranean formation. Many of these subterranean environments are high pressure and high temperature environments. According to an embodiment of the methodology, a capillary electrophoresis system is deployed to a subterranean location. A fluid sample is then obtained and analyzed via the capillary electrophoresis system while at the subterranean location. The capillary electrophoresis system is pressure and temperature controlled at the subterranean location to facilitate accurate analysis of the fluid sample.

Operating the capillary electrophoresis system at the subterranean location enables testing of the fluid sample in the conditions at which it exists at the subterranean location. The in situ testing may reduce pressure and temperature changes that can affect the accuracy of fluid sample testing. For example, the temperature and pressure changes that may occur during removal of the sample to the surface can cause phase separation processes, such as gas separation, precipitation, and/or deposition, where a portion of the dissolved ions in the sample may not reach the sampling point in the dissolved state. Further, the changes may affect the pH value of the sample. The in situ testing reduces pressure and temperature changes that can cause phase separation processes, allowing the fluid sample to be tested in native conditions.

As described in greater detail below, a capillary electrophoresis system is combined with a robust chamber system to enable operation of the capillary electrophoresis system and testing of a variety of fluids in relatively harsh, subterranean locations. In some applications, the testing may be conducted in wellbores on fluids such as oil, gas and/or water. For example, the testing may be performed in a variety of oilfield applications, including well monitoring and testing applications related to monitoring and testing injected and used water composition in enhanced oil recovery (EOR) applications. Additionally, the capillary electrophoresis system may be used at subterranean locations for monitoring fluids stored in deep aquifers. In one example, the capillary electrophoresis system may be used to monitor $CO_2$ sequestration. However, the system and testing methodology may be used to monitor fluid composition in many subterranean environments and applications, within or outside of the oilfield. Further, in certain embodiments, the system and testing methodology may be employed at surface conditions.

Although the overall subterranean testing system may be constructed in various configurations, an example utilizes a capillary electrophoresis system employing a flexible capillary (with or without internal coating) located in tubing that provides mechanical strength. For example, the capillary electrophoresis system may include a silica capillary disposed in metal tubing. However, in other embodiments, the composition and/or structure of the capillary and tubing may vary. The tubing includes inlet and outlet ports for enabling flow of coolant fluid, or other thermal stabilizing fluid, along the capillary to reduce temperature gradients between the walls of the capillary and the interior of the capillary. In some applications, multiple capillaries are provided in parallel to perform different types of tests, or multiple test runs, in a single operation. The capillaries may be designed with narrow bores which encourage rapid heat dissipation. The capillaries also may be formed as flexible capillaries with sufficient flexibility to withstand physical shocks incurred during, for example, deployment to, and operation at, the downhole location. Further, the outer metal tubing may contain a connection point through which information, e.g. test data, from the capillaries may be transmitted to, for example, a surface data acquisition and control system.

The capillary electrophoresis system may be designed for independent operation or for cooperation with other systems. For example, the system may be combined with existing downhole technology for wellbore logging. In another example, the system may be used as a permanent monitoring device in a reservoir or at another subterranean location.

Depending on the specifics of a given application, the testing methodology may be employed for testing a variety of fluids. In many applications, the testing methodology may be used to detect and monitor specific ions or groups of ions. For example, the methodology may be applied downhole to detect ions in the aqueous reservoir fluids, such as cations including, but not limited to, $Li^+$, $Na^+$, $K^+$, $Mg^{2+}$, $Ca^{2+}$, $Sr^{2+}$, $Ba^{2+}$, and $NH_3^+$, among others; anions including, but not limited to, $F^-$, $Cl^-$, $NO_3^-$, $SO_4^{2-}$, $CO_3^{2-}$, $PO_4^{3-}$, $HCO_3^-$, $Br^-$, $I^-$, and $OH^-$, among others; inorganic and organic mercury ions including, but not limited to, $Hg^{2+}$, $Hg^+$, R—Hg, and $R=CH_3-(CH_2)_n$, among others, where R=0, 1, . . . n; organic acids including, but not limited to, naphthenic acids and organic amines, among others; and various metal ions and metals; as well as combinations thereof, for example.

Referring generally to FIG. 1, an embodiment of a fluid testing system is illustrated as deployed in a high pressure and high temperature environment. For example, the testing system may be employed at a subterranean location. In these embodiments, the subterranean location may have a relatively high pressure as compared to a surface pressure (e.g., the subterranean location has a pressure greater than the pressure at the surface). In some applications, the testing system is a subterranean testing system used in a variety of well applications, including onshore applications and offshore applications. However, the testing system may be employed in a variety of other subterranean locations and applications. For purposes of illustration, the testing system is illustrated as deployed to a desired subterranean location via a wellbore but the testing system and methodology should not be construed as limited to well related applications.

In the example illustrated in FIG. 1, a fluid testing system 20 is deployed to a subterranean location 22 located in, for example, a high pressure and high temperature environment. By way of example, the testing system 20 may be deployed to the subterranean location 22 along a wellbore 24 via a suitable conveyance 26. Conveyance 26 may include tubing, cable, wireline, slick line, or another suitable conveyance deployed from a surface location 28, e.g. a land surface or a sea surface. In the illustrated application, subterranean location 22 is within a subterranean formation 30, and testing system 20 is deployed to the formation 30 for testing and/or monitoring of well fluids 32 located in the subterranean formation 30. However, testing system 20 may be used for testing and/or monitoring a variety of other types of fluids in many other types of harsh high-temperature and/or high pressure environments, such as other subterranean environments.

In the embodiment illustrated, fluid testing system 20 includes a capillary electrophoresis system 34 and a chamber system 36 enclosing at least a portion of the capillary electrophoresis system 34. By way of example, the chamber system 36 may include a high-pressure chamber system that enables control over the pressure to which the capillary electrophoresis system 34 is subjected. The chamber system 36 also may be designed to facilitate temperature control with respect to the capillary electrophoresis system 34. In some applications, the capillary electrophoresis system 34 may be designed to output (and/or receive) signals to a data acquisition and control system 38. As illustrated, the data acquisition and control system 38 may be coupled with capillary electrophoresis system 34 via a wired or wireless communication line 40. In the example illustrated, the data acquisition and control system 38 is located at a surface location, however system 38 may be located downhole, at other subterranean locations, at the surface above the subject subterranean location, at a remote surface locations, and/or at multiple locations. Control system 38 may be used to receive and analyze data from fluid sampling system 20 and/or to provide control signals to fluid testing system 20 for controlling the sampling procedure.

Figure 2:
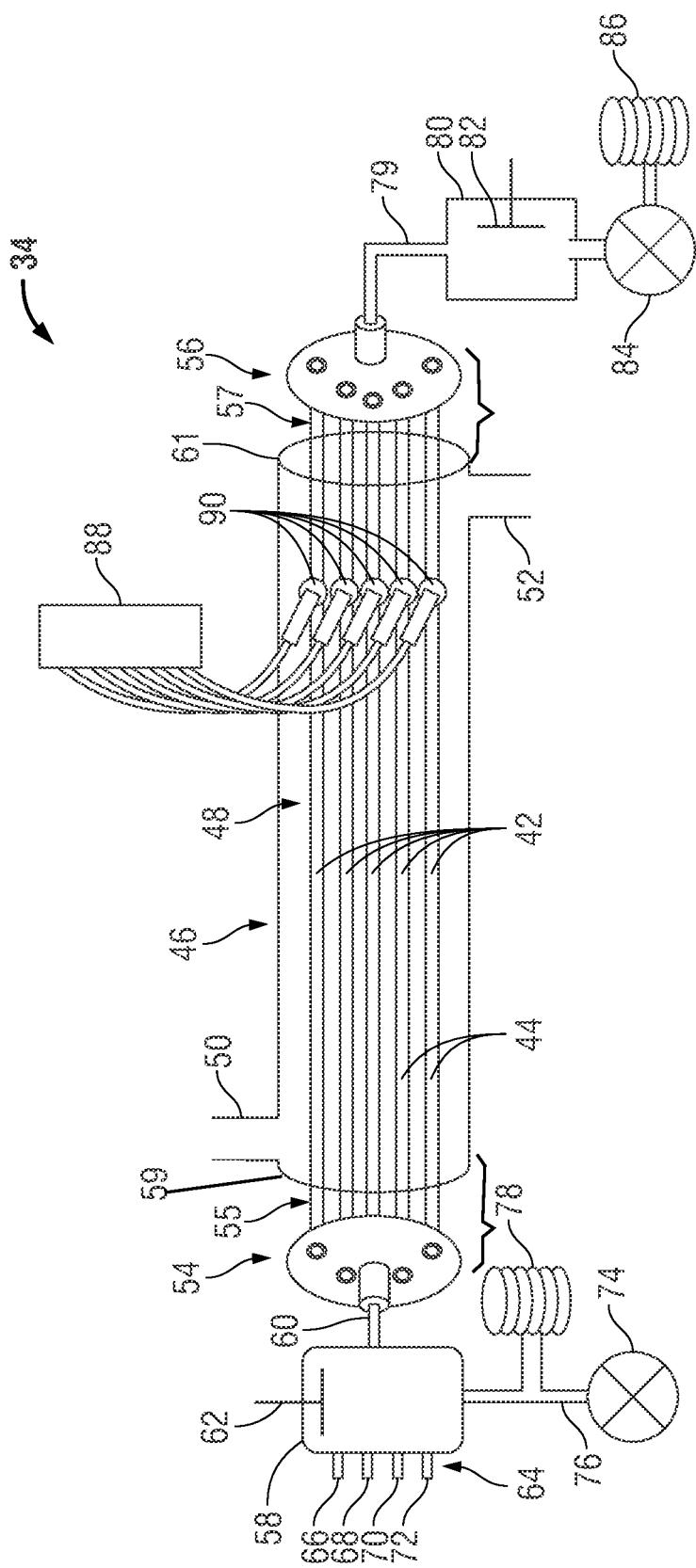
FIG. 2 is a schematic illustration of an example of a capillary electrophoresis system which may be employed at the subterranean location, according to an embodiment of the disclosure.

Referring generally to FIG. 2, an example of capillary electrophoresis system 34 is illustrated. In this embodiment, the capillary electrophoresis system 34 includes one or more capillaries 42, which are shown in FIG. 2 as multiple capillaries disposed in parallel. The capillaries 42 may be formed as flexible capillaries and, in some applications they may be coated internally by a suitable coating 44, which may include a neutral polymer coating, an anionic coating, a cationic coating, a hydrophobic coating, or a hydrophilic coating, among others. Further, the coating 44 may be applied as a static coating, a dynamic coating, or a hybrid coating. The capillaries 42 are disposed within a tubing 46, such as a metal tubing designed to protect the capillaries 42 and to provide a flow path for a thermal stabilizing fluid, such as coolant 48. The tubing 46 includes an inlet 50 and an outlet 52 to direct the flow of coolant 48 along the interior of tubing 46 and to thus control the temperature along capillaries 42 during testing. For example, coolant 48 may be used to dissipate heat generated while applying a voltage across the capillaries 42 to cause ion and/or molecular separations. As the coolant 48 flows through the tubing 46, the coolant 48 may contact the exterior of the capillaries 42 and flow around and past the capillaries 42 to dissipate heat from the capillaries 42.

The coolant 48 may be a fluid, e.g. a liquid, having temperature dependent viscoelastic properties. The viscoelastic properties may be designed to improve the shock resistance of the capillaries 42. For example, the coolant 48 may be able to transform from a high viscosity liquid or an elastic material at lower temperatures into a low viscosity liquid at higher temperatures. In the latter example, the lower temperatures may be experienced when, for example, the fluid testing system 20 is lowered into a wellbore 24 such that the coolant 48 is in an elastic state to protect the capillaries 42 against physical shocks. When at the subterranean location 22, the higher temperature of the location transforms the coolant into the low viscosity fluid to facilitate flow of the coolant 48 through the tubing 46 to cool the capillaries 42.

In the embodiment illustrated, the capillaries 42 are coupled to an inlet multivalve port 54 at an inlet end 55 of the capillaries 42 and to an outlet multivalve port 56 at an outlet end 57 of the capillaries 42. For ease of illustration, the multivalve ports 54 and 56 are shown in an exploded view away from the tubing 46. However, as may be appreciated, the multivalve ports 54 and 56 may be coupled to respective ends 59 and 61 of the tubing 46 to enclose the capillaries 42 within the tubing 46 and to provide an enclosed volume within the tubing 61 for the coolant 48. The multivalve ports 54, 56 enable switching of the fluid testing system 20 from one capillary 42 to another. On the inlet side, multivalve port 54 is coupled to an inlet vessel 58 via a flow passage 60. The inlet vessel 58 may be an anodic chamber having an anode 62. The inlet vessel 58 may receive fluids via fluid supply channels 64 coupled to the inlet vessel 58. By way of example, fluid supply channels 64 may include a sample fluid supply channel 66, a separation buffer fluid supply channel 68, a rinse solution/solvent supply channel 70, and a capillary electrophoresis grade water supply channel 72. As illustrated, inlet vessel 58 also is coupled to a pump 74 via a flow passage 76. The pump 74 may draw fluid from inlet vessel 58 into a reservoir 78 to enable removal and/or storage of excess fluid from inlet vessel 58. As shown in FIG. 2, the reservoir 78 is disposed between the inlet vessel 58 and the pump 74; however, in other embodiments, the reservoir 78 may be disposed on the opposite side of the pump 74 from the inlet vessel 58.

On the outlet side, a flow passage 79 connects outlet multivalve port 56 with an outlet vessel 80 having, for example, a cathode 82. In this example, the outlet vessel 80 serves as a cathodic chamber. Through outlet vessel 80, the outlet multivalve port 56 is connected to a pump 84 and a reservoir 86. The pump 84 and the reservoir 86 may allow flushing and/or rinsing of the capillaries 42 for various applications. As illustrated, the inlet vessel 58 and the outlet vessel 80 are connected to the electrodes, i.e. anode 62 and cathode 82, respectively, to enable electrochemical separation of ions in the sample by applying a voltage across the capillaries 42 containing the fluid sample.

Figure 3:
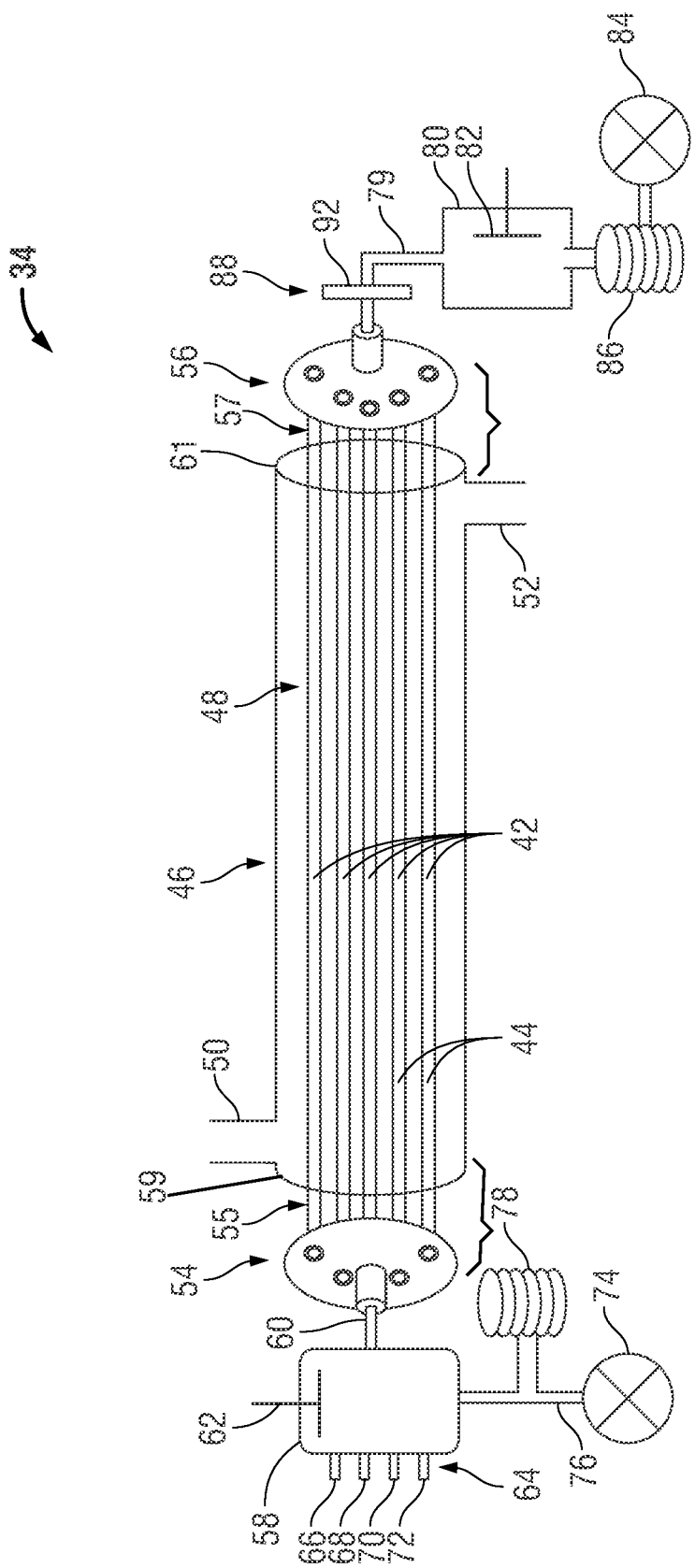
FIG. 3 is a schematic illustration of another example of a capillary electrophoresis system that may be employed at the subterranean location, according to an embodiment of the disclosure.

A detector 88 may be employed to detect migrated ions of the sample being tested. By way of example, the detector 88 may be positioned toward the outlet end 57 of the capillaries 42 for detection of the migrated ions. As illustrated in FIG. 2, the detector 88 may include sensors 90 positioned along a plurality of corresponding capillaries 42. For example, the sensors 90 may be disposed within the tubing 46 on the exterior of the capillaries 42. In certain embodiments, the capillaries 42 may include a window aligned with a UV source or laser of the sensors 90. Moreover, in other embodiments, the sensors 90 may be mounted external to the tubing 46 and aligned with a corresponding window on the tubing 46. Further, in certain embodiments, the sensors 90 may be disposed at least partially within the capillaries 42. In another embodiment, the detector 88 may comprise a single sensor 92 positioned along flow passage 79, as illustrated in the embodiment of FIG. 3. The capillary electrophoresis system 34 depicted in FIG. 3 may operate in a manner similar to that described above with respect to FIG. 2. The detector 88 may have a variety of forms depending on the specifics of a given application. For example, the design of detector 88 may be based on emission or absorption optical or electromagnetic spectroscopic techniques. The design of detector 88 also may be based on electrochemical detectors utilizing conductivity or resistance. Further, the detector 88 may comprise a potentiometric detector.

Figure 4:
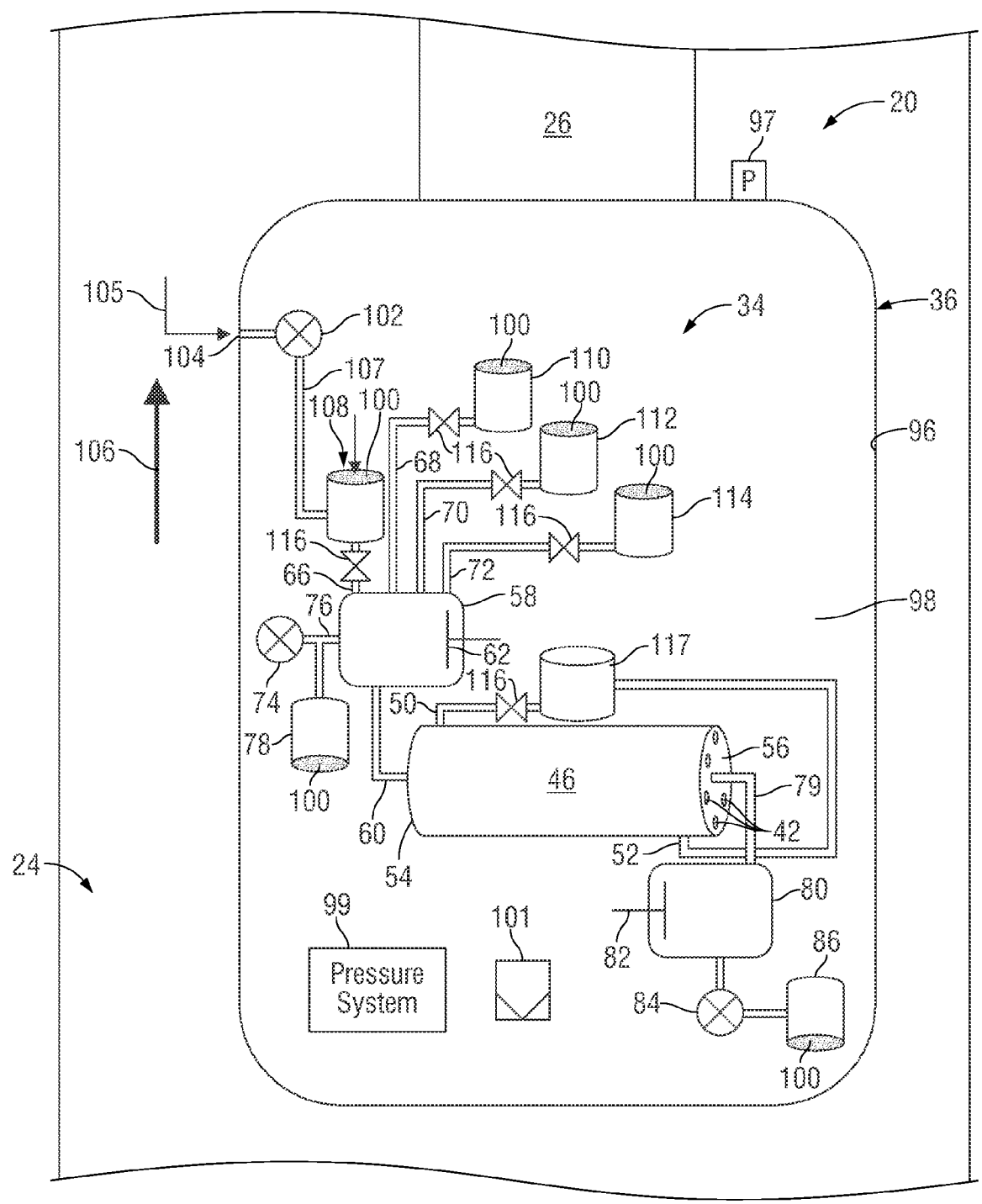
FIG. 4 is a schematic illustration of a capillary electrophoresis system deployed in an example of an enclosed chamber system, according to an embodiment of the disclosure.
Figure 5:
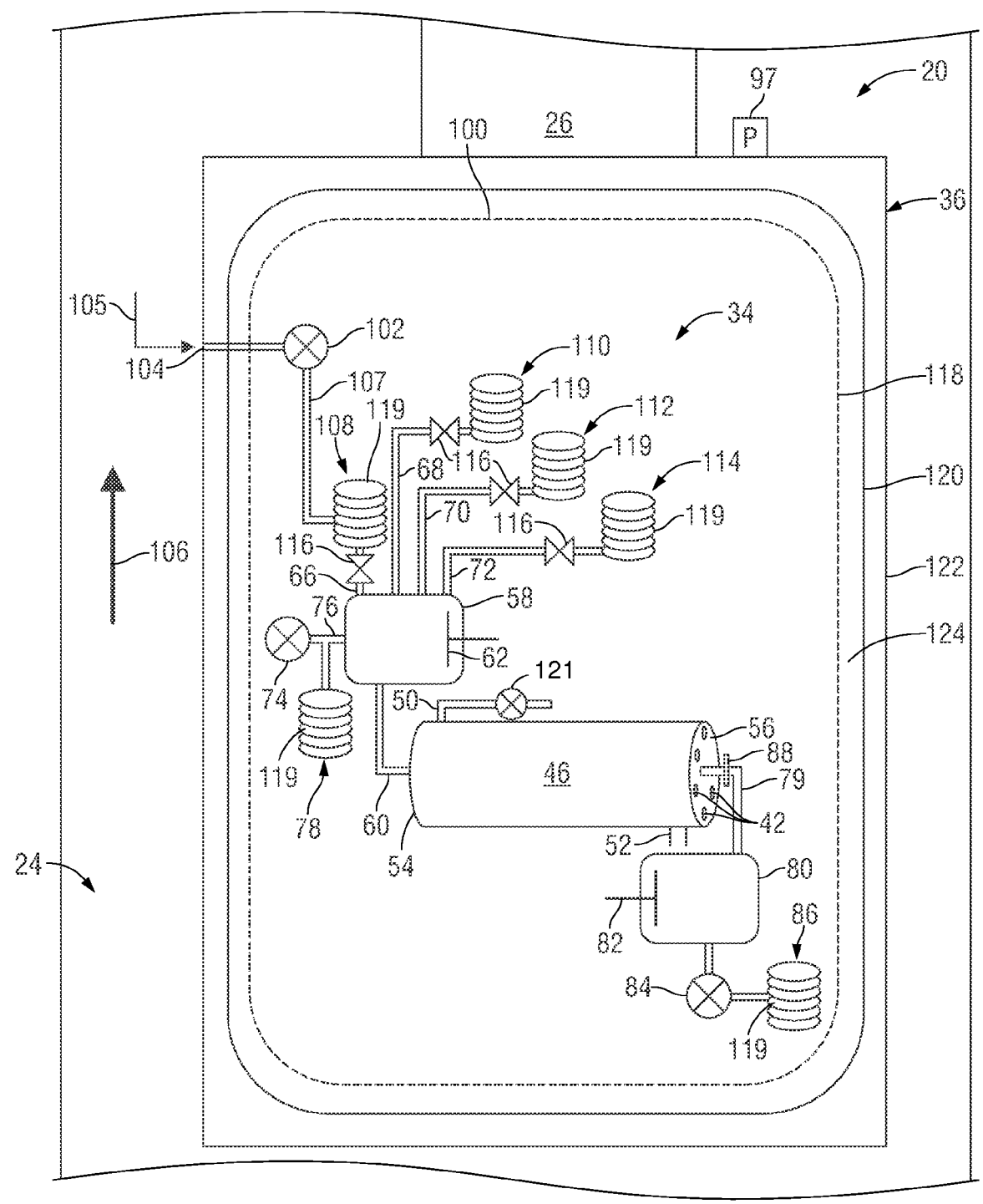
FIG. 5 is a schematic illustration of a capillary electrophoresis system deployed in another example of the enclosed chamber system, according to an embodiment of the disclosure.

Referring generally to FIGS. 4 and 5, embodiments of the capillary electrophoresis system 34 are illustrated in conjunction with chamber system 36. By way of example, chamber system 36 may be an enclosed chamber system, such as a pressure controlled chamber system, enclosing the capillary electrophoresis system 34 in whole or in part. In the examples illustrated in FIG. 4, the chamber system 36 comprises a high-pressure chamber 96 that encloses the capillary electrophoresis system 34 to enable performance of testing operations under subterranean conditions, e.g. reservoir conditions. According to certain embodiments, the high-pressure chamber may be able to withstand pressures as high as approximately 15,000, or more specifically, as high as approximately 20,000 psi. Further, as may be appreciated, the high-pressure chamber 96 also may be designed to operate at lower pressures, including atmospheric pressure, which may enable the fluid testing system 20 to be employed at the surface, as well as at subterranean locations.

In certain applications, the fluid testing system 20 may be pressurized to have a pressure at least slightly greater than the pressure of the surrounding environment. The higher pressure may mitigate depletion of gases from the fluid sample tested via fluid testing system 20. In a wellbore application, for example, the entire fluid testing system 20 (including capillary electrophoresis system 34 and chamber system 36) may be lowered into wellbore 24, and the downhole, subterranean reservoir pressure may be determined. For example, one or more pressure gauges may be disposed in the wellbore 24 and employed to measure the pressure of the wellbore 24 and/or of the subterranean formation 30 (FIG. 1). In certain embodiments, one or more pressure gauges 97 may be included as part of the fluid testing system 20 to measure the pressure in the wellbore 24. Further, in other embodiments, the one or more pressure gauges may be part of a downhole tool, such as a formation pressure tester, that can be lowered into the wellbore 24 along with the fluid testing system 20, or separate from the fluid testing system 20, and employed to measure the wellbore pressure and/or the subterranean formation pressure.

The chamber 96 may then be pressurized to a pressure at least slightly greater than the wellbore pressure. For example, a pressure system 99 may be included within the high pressure chamber 96 and may include a pressure source, such as an inert gas 98 (e.g., a Nobel gas or nitrogen, among others) that can be expelled into the high pressure chamber 96 to pressurize the chamber 96 to a pressure greater than the detected wellbore pressure. In certain embodiments, a controller 101 also may be included within the high pressure chamber 96 to govern operation of the pressure system 99 and to regulate or set the pressure in the chamber 96 to a pressure greater than the detected wellbore pressure. In other embodiments, the pressure system 99 and/or the controller 101 may be external to the chamber 96 (e.g., control system 38) and one or more valves or inlet ports may be employed to direct the inert gas 98 into the chamber 96. For example, the pressure system 99 may be part of a downhole tool that can be lowered into the wellbore 24 along with the fluid testing system 20. In another example, the pressure system 99 may be disposed on the surface and the high pressure chamber 96 may be pressurized prior to lowering the fluid testing system 20 into the wellbore. In this example, the pressure of the wellbore may be detected using a pressure gauge that is lowered into the wellbore prior to lowering the fluid testing system 20 into the wellbore.

The capillary electrophoresis system 34 includes the reservoirs 78 and 86, as well as reservoirs 108, 110, 112, 114, and 117 that hold fluids within the capillary electrophoresis system 34. According to certain embodiments, the reservoirs 78, 86, 108, 110, 112, 114, and 117 may be vessels, such as vials or other suitable containers, supplied with fluids at the surface. Further, in certain embodiments, the reservoirs 78, 86, 108, 110, 112, 114, and 117 may be supplied with fluid when the electrophoresis system 34 is disposed within the wellbore 24. The reservoir 108 may contain sample fluid; the reservoir 110 may contain buffer fluid; the reservoir 112 may contain rinse solution/solvent; the reservoir 114 may contain water, such as capillary electrophoresis grade water; and the reservoir 117 may contain the coolant 48 (FIGS. 2 and 3). The coolant may be circulated from the reservoir 117 through the inlet 50 into the tubing 46 where the coolant may cool the capillaries 42. The coolant may then exit the tubing 46 through the outlet 52 and return to the reservoir 117.

The reservoirs 78, 86, 108, 110, 112, 114, and 117 may be designed to maintain the pressure within the reservoirs at a desired level and uniformity with respect to the capillary electrophoresis system 34. For example, a hydrophobic membrane 100, such as a ceramic or polymeric membrane, may enclose at least a portion of each reservoir 78, 86, 108, 110, 112, 114, and 117 within the capillary electrophoresis system 34. The hydrophobic membrane 100 may be designed to allow gases, such as the inert gas 98 to enter and exit the reservoirs 78, 86, 108, 110, 112, 114, and 117, which may equalize the pressure in the reservoirs 78, 86, 108, 110, 112, 114, and 117 with the pressure in the high pressure chamber 96. Further, the hydrophobic membrane 100 may be designed to retain the fluids within the reservoirs 78, 86, 108, 110, 112, 114, and 117. Accordingly, the pressure of the fluids in the reservoirs 78, 86, 108, 110, 112, 114, and 117 may be maintained at the designated pressure for the high pressure chamber 98.

A fluid sample is drawn into the capillary electrophoresis system 34 through a port 104 in the high pressure chamber 96, as generally shown by an arrow 105. The capillary electrophoresis system 34 includes a pump 102 that draws the sample fluid through a flowline 107 of the capillary electrophoresis system 34 to the sample reservoir 108. The pump 102 enables collection of the sample fluid from a flow stream, such as reservoir flow stream 106 within the wellbore 24. The pump 74 may be operated to draw the sample fluid from the reservoir 108 into the inlet vessel 58, which functions as the anodic chamber. In some applications, the sample fluid is cleaned before delivery to the capillaries 42 for analysis. For example, the sample fluid may be drawn through the supply channel 66 into the inlet vessel 58 and then directed to the reservoir 78, rather than to the capillaries 42, for a certain time prior to beginning the sample operation where the sample fluid is directed through the capillaries 42. Further, in certain embodiments, the supply channel 66 may be connected directly to the flow passage 60, allowing the sample fluid to bypass the inlet vessel 58.

The pump 74 also may be employed to draw the fluid from the reservoirs 110, 112, and 114 into the inlet vessel 58. Valves 116 may be disposed within the fluid supply channels 66, 68, 70, and 72 and actuated to determine the fluid that is drawn into the inlet vessel 58 by the pump 74. In particular, the valve 116 for the desired fluid may be opened while the other valves 116 are closed. For example, to draw the sample fluid from the sample reservoir 108 into the inlet vessel 58, the valve 116 in the supply channel 66 may be opened while the other valves 116 are closed. In certain embodiments, a controller 101 may be disposed within the fluid testing system 20 or at the surface (e.g., control system 38) to govern operation of the valves 116 and/or the pumps 74, 84, and 102. The fluids from the inlet vessel 58 is then drawn through the desired capillary or capillaries 42 under the influence of an electric field (e.g., generated by the anode 62 and cathode 82) and/or with motive force generated by the pump 84.

To inhibit depletion of dissolved gases from the sample fluid, the sample fluid may be directed through a diffusion path to pressure equilibrate the sample fluid with the pressure in the high pressure chamber 96. According to certain embodiments, the flow passage 107 may be a long capillary tube or a column filled with inert fibers or other porous materials. In certain embodiments, the flow passage 107 may include one or more filters, such as inert fibers or other filters, designed to remove contaminants, such as debris or other large particles, from the sample fluid. As the sample fluid flows through the passage 107, the fluid sample may be pressurized by the inert gas 98 within the chamber 96. Further, the diffusion path (e.g., the capillary tube or inert fibers) may discourage depletion of dissolved gasses from the fluid sample. Accordingly, the sample fluid may be pressure equilibrated while chemical equilibration is hindered. Moreover, in certain embodiments, the pressure within the high pressure chamber 96 may be set to a pressure greater than the wellbore pressure, which may also discourage depletion of dissolved gases from the sample fluid.

Referring generally to FIG. 5, another embodiment of the chamber system 36 is illustrated. The chamber system 36 includes the pumps 74, 84, and 102, the valves 116, the fluid supply channels 66, 68, 70, and 72, the vessels 58 and 80, the port 104, and the one or more pressure sensors 97 that function in a manner similar to that described above with respect to FIG. 4. However, in this embodiment, rather than a gas filled chamber 96, the chamber system 36 is an enclosed chamber system that includes an impound enclosure 118 that surrounds the components of the capillary electrophoresis system 34. The impound enclosure 118 is enclosed by a bellows container 120 which, in turn, is enclosed by a solid container 122, which may be a high pressure chamber. The reservoirs 78, 86, 108, 110, 112, and 114 include bellows features 119 that allow the reservoirs 78, 86, 108, 110, 112, and 114 to expand and contract to equilibrate pressure of the fluids within the reservoirs 78, 86, 108, 110, 112, and 114 with the pressure in the bellows container 120. According to certain embodiments, the bellows features 119 may include walls of the reservoirs 78, 86, 108, 110, 112, and 114 that are flexible and designed to expand and contract in response to pressure changes. The reservoirs 78, 86, 108, 110, 112, and 114 may be partially or entirely constructed of the bellows features 119.

The bellows container 120, as well as the various bellows features 119, can be expanded and contracted to maintain the designated pressure within the capillary electrophoresis system 34. In this embodiment, the capillary electrophoresis system 34 may be enclosed, e.g. caged, within impound enclosure 118, which is positioned within the bellows container 120. According to certain embodiments, the impound enclosure 118 may be a mesh or wire cage that structurally protects the components of the capillary electrophoresis system 34 when the bellows container 120 contracts.

Accordingly, the impound enclosure 118 may limit contraction of the bellows container 120 so that the bellows container 120 does not contact the components of the capillary electrophoresis system upon contraction.

The bellows container 120 may be filled with a coolant 124, e.g. a coolant solution or viscoelastic fluid, designed to maintain a uniform pressure within the capillary electrophoresis system 34. For example, the coolant 124 may be designed to balance changes in pressure and temperature caused by sample fluid entering the capillary electrophoresis system 34 through the port 104. The coolant 124 also may be employed as the coolant 48 (FIG. 3) that cools the capillaries 42. For example, a pump 121 may be employed to circulate the coolant 124 through the inlet 50 into the tubing 46 where the coolant 124 may cool the capillaries 42. The coolant 124 may then exit the tubing 46 through the outlet 52 and return to the interior of the bellows container 120. The impound enclosure 118 may be designed so that the coolant 124 can pass through the enclosure 118 to circulate around the components of the capillary electrophoresis system 34.

Figure 6:
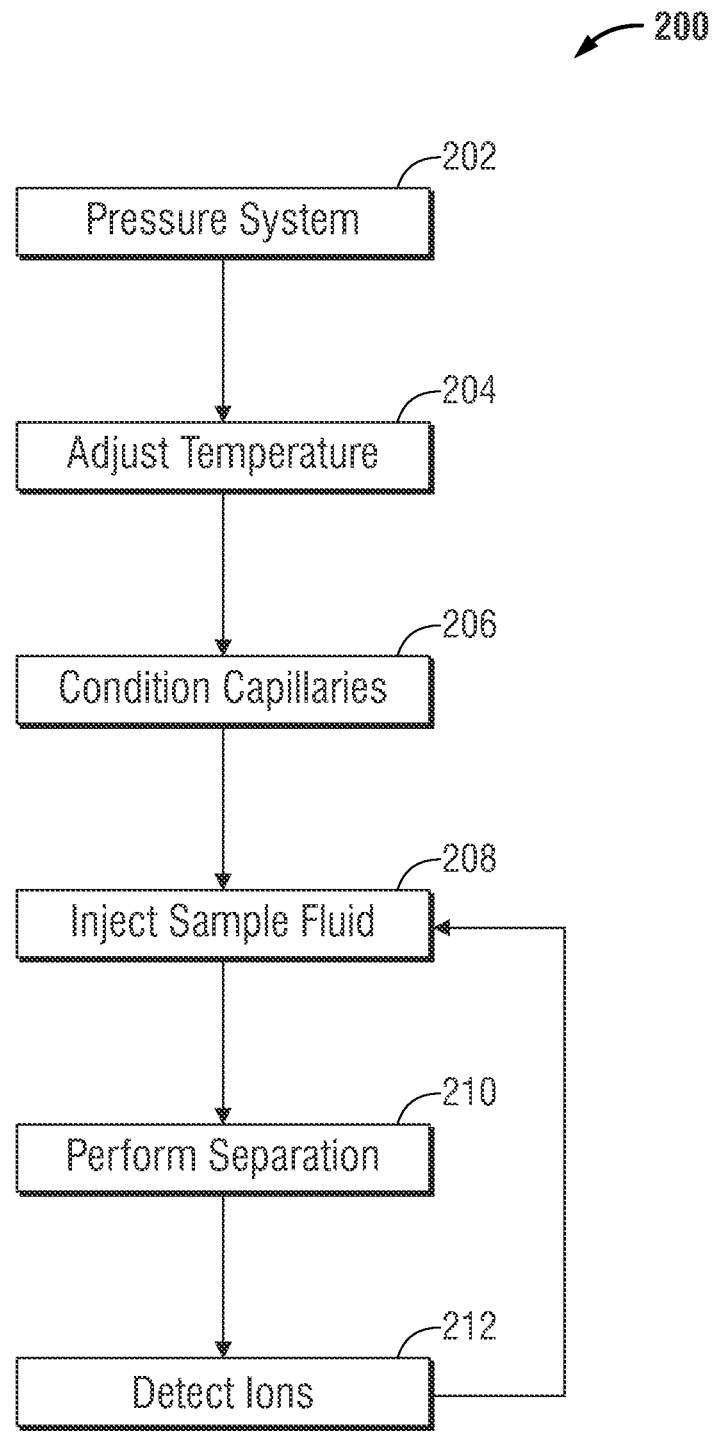
FIG. 6 is a flow chart of a method for operating a fluid testing system, according to an embodiment of the disclosure.

FIG. 6 depicts a method 200 for operating the capillary electrophoresis system 34. The method 200 may begin by pressurizing (block 202) the capillary electrophoresis system 34. For example, the fluid testing system 20 may be deployed to a subterranean location, e.g. a wellbore location. The pressure of the capillary electrophoresis system 34 may then be increased to a pressure approximately equal to or slightly greater than the pressure at the subterranean location. For example, as shown in FIG. 4, the pressure system 99 may be employed to adjust the level of inert gas 98 within the vessel 96. In another example, as shown in FIG. 5, the coolant 124 may increase in temperature as the capillary electrophoresis system 34 is deployed to the subterranean location, which in turn may increase the pressure within the bellows container 120. In other embodiments, the capillary electrophoresis system 34 may be pressurized at the surface, prior to deployment to the subterranean location.

The temperature of the capillaries may then be adjusted (block 204) to a temperature suitable for capillary electrophoresis. For example, as shown in FIGS. 2 and 3, the coolant 48 may be circulated through the tubing 46 to adjust the temperature of the capillaries 42 to the desired temperature. After the desired temperature is reached, one or more designated capillaries 42 are prepared for measurement by performing capillary conditioning (block 206). Various conditioning procedures known in the art may be conducted to condition the capillaries. For example, one or more capillaries 42 may be rinsed with rinse solution, separation buffer, and high purity water from the reservoirs 110, 112 and 114, respectively. In some applications, the capillaries 42 may be coated with an anionic or cationic surfactant or any other selective material for specific applications. For example, the internal coating 44 (FIG. 3) may include anionic or cationic surfactants. In certain embodiments, additional reservoirs that contain different types of coatings may be disposed within the capillary electrophoresis system 34. The coatings may be selected based on subterranean conditions and fluid properties and may be directed to the capillaries using additional fluid supply channels 64 and the multivalve ports 54 and 56, as described above with respect to FIGS. 2 and 3. In other embodiments, certain capillaries 42 may be coated with different types of coatings 44 prior to disposing the capillary electrophoresis system 34 at the subterranean location. In these embodiments, the capillaries may be conditioned at the surface, prior to sending the fluid testing system 20 downhole, or to another subterranean location.

The capillaries 42 that have the desired type of coating (e.g., based on downhole conditions and/or downhole fluid properties) may be selected and conditioned using the multivalve ports 54 and 56.

After the capillaries 42 are conditioned, sample fluid may be injected (block 208) into the one or more capillaries 42. For example, the valve 116 disposed in the sample supply channel 66 may be opened to direct sample fluid from sample reservoir 108 into the inlet vessel 58. The valve ports 54 and 56 also may be set to direct the sample fluid from the inlet vessel 58 through certain capillaries 42 and into the outlet vessel 80. As described above with respect to FIGS. 2-5, the pump 74 may be employed to draw sample fluid through the capillaries 42. In certain embodiments, a single capillary 42 may be filled with sample fluid, while in other embodiments, multiple capillaries 42 may be filled with sample fluid for multi-channel operation. For example, the sample fluid may be routed through two or more capillaries 42 in parallel, and these capillaries may have the same or different types of coatings 44 and/or conditioning. After the sample fluid is directed into the capillaries 42, water may be injected into the capillaries 42 as a water cap. For example, the valve 116 disposed in water channel 72 may be opened to direct water from the water reservoir 114 into the capillaries 42.

Capillary electrophoresis may then be performed (block 210) to separate ions within the sample fluid. For example, the inlet vessel 58 may be filled with separation buffer fluid and voltage may be applied across the capillaries 42 to promote electrochemical separation of the ions. In certain embodiments, multiple types of buffer fluids may be included within reservoirs disposed in the capillary electrophoresis system 34. Different buffer fluids may be employed depending on the type of sample fluid and ions of interest. The valve 116 disposed in the separation buffer channel 68 may be opened to direct the selected separation buffer fluid from the reservoir 110 into the inlet vessel 58.

Under the influence of the electric field established by the voltage, ions may separate based on their charge and on their size. Cations followed by neutrals and anions move towards the cathode 82. (It should be noted the voltage may be supplied from various power sources, such as a surface power source or a battery located in chamber system 36.) The ions may then be detected (block 212) by the detector 88 (FIGS. 2 and 3) as the ions move toward the outlet end of the capillary 42. According to certain embodiments, the detector 88 may be employed to determine the type and/or amount of ions in the sample fluid. During capillary electrophoresis, the temperature within the capillaries 42 may be controlled by circulating the coolant 48 through the tubing 46, as described above with respect to FIG. 2. Further, the pressure acting on capillary electrophoresis system 34 may be balanced to equilibrium or to a desired small pressure differential with respect to the surrounding pressure, e.g. reservoir pressure. For example, using the pressure system 99 described above with respect to FIG. 4 or the bellows containers 119 and 120 described above with respect to FIG. 5.

Once the ions have been detected, parts of the method 200 may be repeated to detect additional ions within the sample fluid. For example, the sample fluid may be injected (block 208) into other capillaries 42 to separate different ions within the sample fluid during an additional test. In certain embodiments, the sample fluid may be injected into capillaries 42 that have a different internal coating 44 from the capillaries used in the previous test. Further, a different separation buffer fluid may be employed. In other embodiments, the previously used capillaries 42 may again be conditioned (block 206) prior to injecting (block 208) the sample fluid for an additional test.

The design and operation of the fluid testing system 20 enables reservoir fluid analysis with a subterranean, highly sensitive capillary electrophoresis technique. The capillary electrophoresis 34 is protected by enclosed chamber system 94 for operation under high temperature and high pressure conditions, such as those found in many subterranean environments including downhole reservoir environments. The fluid testing system 20 also provides thermal control under reservoir conditions which, in turn, facilitates reproducibility and reliability of the measurements.

The capillaries 42 may be constructed as narrow bore capillaries able to dissipate heat efficiently. Further, a multichannel arrangement utilizing multiple capillaries 42 enables the running of multiple measurements in a single operation. Constructing the capillaries 42 as flexible capillaries also provides additional ruggedness to the entire fluid sampling system 20 for a variety of subterranean operations. The use of enclosed chamber system 94 enables analysis of reservoir fluids and other subterranean fluids under harsh subterranean conditions while inhibiting composition change of the fluid sample due to phase separation, scaling, deposition, or the occurrence of other events.

Depending on the environmental conditions and on the parameters of a given sample testing operation, the overall fluid testing system may utilize a variety of components and component configurations. For example, the chamber system may utilize a variety of membranes, bellows containers, and/or other types of enclosures formed of a variety of materials. Similarly, the capillary electrophoresis system may utilize a variety of pumps, reservoirs, vials, chambers, electrodes, coolants, capillaries, and/or other components arranged in various numbers and configurations. The bellows containers may employ a variety of bellows materials and structures. The fluid testing system may be employed in well-related reservoir applications, in subterranean caverns, in subterranean flow networks, and in various other subterranean environments. Further, the fluid testing system and methodology may be used in other high pressure and high temperature applications to enable fluid testing under those relatively harsh conditions.

Although a few embodiments of the disclosure have been described in detail above, those of ordinary skill in the art will readily appreciate that many modifications are possible without materially departing from the teachings of this disclosure. Accordingly, such modifications, as well as functionally equivalent structures, methods, and uses, are intended to be included within the scope of this disclosure as defined in the claims.

What is claimed is:

1. A method for fluid testing, comprising:
   lowering a fluid testing system into a wellbore extending into a subterranean location;
   pressurizing the fluid testing system, disposed at the subterranean location, to a high pressure compared to a surface pressure, the fluid testing system comprising a capillary electrophoresis system and one or more test fluid reservoirs, wherein the capillary electrophoresis system includes a plurality of capillaries;
   directing test fluid from the one or more test fluid reservoirs into at least one capillary of the plurality of capillaries to condition the at least one capillary;
   directing sample fluid into the plurality of capillaries for testing while at the subterranean location;
   using the capillary electrophoresis system to perform capillary electrophoresis testing on the sample fluid at the subterranean location, wherein certain capillaries of the pluralities of capillaries are coated with different types of coatings such that the plurality of capillaries perform different types of tests during the capillary electrophoresis testing; and
   wherein pressurizing the fluid testing system comprises controlling pressure of fluid in a chamber that encloses the fluid testing system.

2. The method as recited in claim 1, wherein pressurizing the fluid testing system comprises directing a gas into the chamber enclosing the fluid testing system.

3. The method as recited in claim 1, wherein the chamber enclosing the fluid testing system comprises a bellows container filled with fluid, and pressurizing the fluid testing system comprises contracting the bellows container.

4. The method as recited in claim 1, wherein directing sample fluid comprises directing the sample fluid from a reservoir that includes a hydrophobic membrane.

5. The method as recited in claim 1, wherein directing sample fluid comprises directing the sample fluid from a reservoir that includes a bellows feature.

6. The method as recited in claim 1, wherein directing sample fluid comprises operating a multi-valve inlet port coupled to each of the plurality of capillaries to direct the sample fluid into a selected one of the plurality of capillaries.

7. The method as recited in claim 1, wherein the capillary electrophoresis involves applying a voltage across the plurality of capillaries to cause electrochemical separation of ions within the sample fluid and migration of such ions through the plurality of capillaries.

8. The method as recited in claim 1, comprising circulating a thermal stabilizing fluid through a tube enclosing the plurality of capillaries.

9. A fluid testing system, comprising:
   a capillary electrophoresis system comprising a plurality of capillaries configured to receive sample fluid, wherein certain capillaries of the pluralities of capillaries are coated with different types of coatings such that the plurality of capillaries perform different types of tests during capillary electrophoresis testing;
   one or more test fluid reservoirs in fluid communication with the capillary electrophoresis system; and
   a fluid-filled chamber enclosing the capillary electrophoresis system, wherein the fluid-filled chamber is configured to pressurize the capillary electrophoresis system by controlling pressure of fluid in the fluid-filled chamber.

10. The fluid testing system of claim 9, wherein the capillary electrophoresis system further comprises an inlet multivalve port and an outlet multivalve port coupled to opposite ends of the plurality of capillaries.

11. The fluid testing system of claim 10, wherein the capillary electrophoresis system further comprises a coolant flow tube enclosing the capillaries and extending between the inlet multivalve port and the outlet multivalve port.

12. The fluid testing system of claim 9, wherein the one or more test fluid reservoirs have a pressure balancing feature which comprises a hydrophobic membrane to permit gas within the chamber to enter the one or more test fluid reservoirs.

13. The fluid testing system of claim 9, wherein the one or more test fluid reservoirs have a pressure balancing feature which comprises a bellows to permit contraction and expansion of the one or more test fluid reservoirs.

14. The fluid testing system of claim 9, wherein the fluid-filled chamber comprises a bellows container filled with fluid.

15. The fluid testing system of claim 9, further comprising a pressure system configured to direct a gas into the chamber.

16. The fluid testing system of claim 9, comprising a pressure gauge configured to measure an external pressure exerted on the fluid testing system and a controller configured to set an internal pressure within the chamber based on the external pressure.

17. The fluid testing system of claim 9, comprising a port disposed in the chamber to direct the sample fluid into the chamber.

18. The fluid testing system of claim 9, wherein the certain capillaries are coated with different types of coatings prior to disposing the capillary electrophoresis system at a subterranean location.

19. The fluid testing system of claim 9, wherein the test fluid reservoirs contain the different types of coatings, and such coatings are applied to the certain capillaries as part of conditioning of the plurality of capillaries.

20. The fluid testing system of claim 19, wherein the coatings are applied to the certain capillaries as part of conditioning of the plurality of capillaries based on downhole conditions and/or downhole fluid properties.

21. The fluid testing system of claim 9, wherein the test fluid reservoirs contain test fluids selected from the group consisting of rinse solution, solvent, separation buffer, high purity water, coolant, and capillary coatings (such as anionic and cationic surfactants).

22. The fluid testing system of claim 9, wherein a thermal stabilizing fluid is used to control temperature of the plurality of capillaries and to protect the plurality of capillaries against physical shocks.

23. The fluid testing system of claim 9, wherein the capillary electrophoresis system includes an inlet vessel having an anode, an outlet vessel having a cathode, the plurality of capillaries fluidly coupled between the inlet vessel and the outlet vessel, and a detector configured to detect ions that undergo electrochemical separation and migration through the plurality of capillaries under the influence of a voltage across the capillaries provided by the anode and cathode.

24. The method as recited in claim 1, wherein the certain capillaries are coated with different types of coatings prior to disposing the capillary electrophoresis system at the subterranean location.

25. The method as recited in claim 1, wherein the test fluid reservoirs contain the different types of coatings, and such coatings are applied to the certain capillaries as part of conditioning of the plurality of capillaries.

26. The method as recited in claim 25, wherein the coatings are applied to the certain capillaries as part of conditioning of the plurality of capillaries based on downhole conditions and/or downhole fluid properties.

27. The method as recited in claim 1, wherein the test fluids contained in the test fluid reservoirs are selected from the group consisting of rinse solution, solvent, separation buffer, high purity water, coolant, and capillary coatings (such as anionic and cationic surfactants).

28. The method as recited in claim 1, wherein a thermal stabilizing fluid is used to control temperature of the plurality of capillaries and to protect the plurality of capillaries against physical shocks.

29. The method as recited in claim 1, wherein the capillary electrophoresis system includes an inlet vessel having an anode, an outlet vessel having a cathode, the plurality of capillaries fluidly coupled between the inlet vessel and the outlet vessel, and a detector configured to detect ions that undergo electrochemical separation and migration through the plurality of capillaries under the influence of a voltage across the capillaries provided by the anode and cathode.

30. The method as recited in claim 29, wherein:
the detector includes a plurality of sensors positioned along the plurality of capillaries.

31. The method as recited in claim 30, wherein:
the sensors are disposed within tubing on the exterior of the capillaries; and/or
the capillaries include a window aligned with a UV source or laser of the sensors; and/or
the sensors are mounted external to tubing that carries thermal fluid and aligned with a corresponding window on the tubing; and/or
the sensors are disposed at least partially within the capillaries.

32. The method as recited in claim 29, wherein the detector comprises a single sensor.

33. The method as recited in claim 29, wherein the operation of the detector is based on a spectroscopic technique involving emission or absorption of an optical or other electromagnetic signal.

34. The method as recited in claim 29, wherein the operation of the detector is based on an electrochemical technique involving conductivity or resistance or potentiometry.

35. The method as recited in claim 1, wherein the plurality of capillaries are selected and conditioned using at least one multivalve port.

36. The method as recited in claim 1, wherein the different types of tests performed during the capillary electrophoresis detect cations and anions in a reservoir fluid.

37. The method as recited in claim 36, wherein:
the detected cations are selected from the group consisting of $Li^+$, $Na^+$, $K^+$, $Mg^{2+}$, $Ca^{2+}$, $Sr^{2+}$, $Ba^{2+}$, $NH_3^+$, $Hg^+$, $Hg^{2+}$ and combinations thereof; and/or
the detected anions are selected from the group consisting of $F^-$, $Cl^-$, $NO_3^-$, $SO_4^{2-}$, $CO_3^{2-}$, $PO_4^{3-}$, $HCO_3^-$, $Br^-$, $I^-$, $OH^-$, and combinations thereof; and/or
the detected cations and anions include inorganic and organic mercury ions; and/or
the detected cations and anions include mercury ions; and/or
the detected cations and anions include mercury ions selected from the group consisting of $Hg^{2+}$, $Hg^+$, R—Hg with R=$CH_3$—$(CH_2)_n$, and combinations thereof; and/or
the detected cations and anions include organic acids; and/or
the detected cations and anions include organic acids selected from the group consisting of naphthenic acids and organic amines; and/or
the detected cations and anions include metal ions.

38. The method as recited in claim 1, wherein the plurality of capillaries are formed as flexible capillaries.

39. The method as recited in claim 1, wherein the plurality of capillaries are silica capillaries.

* * * * *